United States Patent [19]
Almstedt et al.

[11] Patent Number: 5,831,026
[45] Date of Patent: Nov. 3, 1998

[54] PROCESS FOR PURIFYING FACTOR VIII

[75] Inventors: Annelie Almstedt, Spånga; Helena Sandberg, Bromma; Anna-Lisa Smeds, Sollentuna; Maria Wrangel, Vällingby; Anna Östlin, Stockholm, all of Sweden

[73] Assignee: Pharmacia & Upjohn AB, Stockholm, Sweden

[21] Appl. No.: 809,756

[22] PCT Filed: Nov. 14, 1995

[86] PCT No.: PCT/SE95/01351

§ 371 Date: May 30, 1997

§ 102(e) Date: May 30, 1997

[87] PCT Pub. No.: WO96/15150

PCT Pub. Date: May 23, 1996

[30] Foreign Application Priority Data

Nov. 14, 1994 [SE] Sweden .................................. 9403915

[51] Int. Cl.$^6$ .......................... A61K 35/14; A61K 38/46; A23J 1/00
[52] U.S. Cl. .......................... 530/383; 530/413; 530/416; 530/417; 530/427; 530/830; 530/831; 424/94.67; 424/529; 424/532; 435/183; 435/184; 514/2; 514/6; 514/21
[58] Field of Search .................... 530/383, 413, 530/416, 417, 427, 830, 831; 424/94.67, 529, 532; 435/183, 184; 514/2.61, 21

[56] References Cited

U.S. PATENT DOCUMENTS

| | | |
|---|---|---|
| 4,406,886 | 9/1983 | Bier et al. ................................. 424/101 |
| 5,149,787 | 9/1992 | Kunicki et al. .......................... 530/383 |
| 5,278,289 | 1/1994 | Johnson et al. .......................... 530/383 |
| 5,424,401 | 6/1995 | Heimburger et al. ................... 530/383 |

FOREIGN PATENT DOCUMENTS

| | | |
|---|---|---|
| 0160457 | 11/1985 | European Pat. Off. . |
| 0197901 | 10/1986 | European Pat. Off. . |
| WO 9002175 | 3/1990 | WIPO . |
| WO90/02175 | 3/1990 | WIPO . |
| WO 9005719 | 5/1990 | WIPO . |
| WO 9109122 | 6/1991 | WIPO . |
| WO 9310143 | 5/1993 | WIPO . |
| WO 9324137 | 12/1993 | WIPO . |

OTHER PUBLICATIONS

Ole Nordfolng et al. *Generation of Active Coagulation Factor VIII from Isolated Subunits*, The Journal of Biological chemistry, Vol. 263, No. 3, pp. 1115–1118 (1988).

Ikegawa et al, *Biochemical and Biophysical Research Communications*, vol. 171, No. 2, pp. 669–675 (1990).

W. I. Wood et al, *Expression of Active Human Factor VIII from Recombinant DNA Clones*, Nature, vol. 312, 22 Nov. 1984.

J. S. Bond et al, *Mammalian Metalloendopeptidase*; Int. J. Biochem., vol. 17, No. 5, pp. 565–574 (1985).

Andersoon et al, *Isolation and Characterization of Human Factor VIII: Molecular Forms in Commercial Factor VIII Concentrate, Cryoprecipitate, and Plasma*, Proc. Natl. Acad. Sci., vol. 83, pp. 2979–2983, May 1986).

P.J. Fay et al, *Characterization of the Interaction Between the A2 Subunit and A1/Ae–C1–C2 Dimer in Human Factor Viiia*, The Journal of Biological Chemistry , vol. 267, No. 19, pp. 13246–13250 (Jul. 5, 1992).

N. Bihoreau et al, *Copper–atom Identification in the Active Forms of Plasma–Derived FVIII and Recombinant FVIII— III*, Eur. J. Biochem, 222, 41–48 (1994).

A. Barrett, *Proteolytic Enzymes: Asparatic and Metallo Peptidases Methods In Enzymology*, vol. 248, pp. 263–283 (1995).

Janson et al, *Protein Purification: Principles, High Resolution Methods, and Applications*, pp. 3–11 1989).

H. Birkedal–Hanset et al, *Matrix Metalloproteinases: A Review*, Critical Reviews in Oral Biology and Medicine, 4(1):197–250 (1993).

N. Nishio et al, *Peptide Hydroxamic Acids as Inhibitors of Thermolysin*, Biochemistry, vol. 17, No. 14, pp. 2846–2850 (1978).

Pharmacia LKB Biotechnology, *Technical Note BioProcess™Media*, "Sepharose®Fast Flow Ion Exchangers" (No publication date available).

Pharmacia Fine Chemicals AB, "DEAE–Sepharose®Fast Flow, CM–Sepharose Fast Flow" (No publication date available).

Pharmacia BioProcess Technology, *Data File 3200, Ion Exchange Media*, "Q&SP Sepharose®High Performance BioProcess Media," 1992.

KabiVitrum AB, "*Coatest*®On–line Factor VIII Kit, Adaptation to Microtiter Technique," pp. 1–13, 1984.

Kabi Vitrum AB (1984), "Determination of factor VIII:C activity in micrototerplates using the chromogenic COAT-EST Factor VIII kit," 1984.

Sartonius Catalogue (1992), "Sartobind Minisart®Membrane Absorbers".

Tibtech (1986) "*Mini–Leak*®*Vinylsulfone Agarose*, A New and Easy Activated Gel for Preparation of Stable Immunoabsorbents and Affinity Matrices", pp. 8–9.

Kem–En–Tec Resourceful Science, *Instruction Manual: Mini* Leak, pp. 1–10 (No publication date available).

Lihme et al (1986), *Journal of Chromatography*, vol. 376, pp. 299–305.

*Primary Examiner*—Cecilia J. Tsang
*Assistant Examiner*—Abdel A. Mohamed
*Attorney, Agent, or Firm*—Dinsmore & Shohl LLP

[57] ABSTRACT

A process for reducing degradation of recombinant coagulation factor VIII caused by metal-dependent proteases requiring $Zn^{2+}$ for activity or containing $Zn^{2+}$ as an integral part of their structure comprises adding an inhibitor of $Zn^{2+}$ dependent proteases to a recombinant factor VIII solution. The recombinant factor VIII solution is obtained after harvesting a conditioned medium from a cell culture used for producing the recombinant coagulation factor VIII. The inhibitor is selected from complexing agents with a stronger affinity for the $Zn^{2+}$ ion of the protease than for the ion or ions stabilizing the factor VIII molecule, and compounds structurally related to the natural substrate of the protease and containing an electronegative moiety.

25 Claims, No Drawings

PROCESS FOR PURIFYING FACTOR VIII

FIELD OF THE INVENTION

Proteases generally tend to reduce the activity of coagulation factor VIII by degrading the molecule. The present invention relates to a process for reducing the detrimental influence of metal-dependent proteases upon recombinant factor VIII molecules, by adding an inhibitor of metal-dependent proteases to a solution after harvest. The solution is suitably the harvest solution or any aqueous solution being fed to or leaving the primary isolation, being the initial step of the purifying sequence. The inhibitor is selected from i) complexing agents with a stronger affinity for the alkaline-earth metal ion or metal ion of the protease than for the ion or ions stabilizing the factor VIII molecule and ii) compounds structurally related to the natural substrate of the protease and containing an electronegative moiety. The presence of an inhibitor, preferably a complexing agent, after harvest allows for a prolonged harvest period and considerably higher yield with essentially retained factor VIII activity. The invention further relates to an aqueous solution containing recombinant factor VIII which has been purified according to the present process and use of such an aqueous solution, for the manufacture of a medicament for administration to a patient having the symptoms of hemophilia. Also, the invention relates to a method for treatment of hemophilia by administration of a therapeutically effective amount of recombinant factor VIII which has been purified according to the present process.

BACKGROUND OF THE INVENTION

Hemophilia is an inherited disease which has been known for centuries, but it is only within the last four decades that it has been possible to differentiate between the various forms; hemophilia A and hemophilia B. Hemophilia A is the most frequent form. It affects only males with an incidence of one or two individuals per 10 000 live-born males. The disease is caused by strongly decreased level or absence of biologically active coagulation factor VIII (antihemophilic factor), which is a protein normally present in plasma. The clinical manifestation of hemophilia A is a strong bleeding tendency and before treatment with factor VIII concentrates was introduced, the mean age of the patients concerned was less than 20 years. Concentrates of factor VIII obtained from plasma have been available for about three decades. This has improved the situation for treatment of hemophilia patients considerably and offered them the possibility of living a normal life.

Until recently, therapeutic factor VIII concentrates have been prepared by fractionation of plasma. However, there are since some years methods available for production of factor VIII in cell culture using recombinant DNA techniques as reported in e.g. W. Wood et al, Nature, 312, p. 330–37 (1984) and EP-A-0 160 457.

It is well known that proteins are cleaved by proteases, such as serine, cysteine, aspartic and metallo proteases. Many proteases need alkaline-earth metals or metals (in the following just denoted metals) for their activity. The metal-dependent proteases are either considered to be metal-activated proteases (to which metal ions must be added for activity) or metallo proteases (which contain metals as an integral part of their structure). Concerning the first group, activation and stabilization of enzymes by metals frequently occur in several classes of proteases, such as serine and cysteine proteases.

The importance of a metallo protease in cultured endothelial cells for the secretion of a certain metabolite has been shown by R. Ikegawa et al in Biochem. Biophys. Res. Comm. 171(2), p. 669–675 (1990). This was revealed by the suppressing effect on this secretion recognized by the addition of a metallo protease specific inhibitor. It was evident, however, that the enzyme was confined to the intracellular space, since no effect of the inhibitor was obtained in a cell-free conditioned medium.

The effect of proteases are though far more often mentioned in the context of the potential risk of degradation of the protein at issue.

U.S. Pat. No. 5,149,787 (The Blood Center Research Foundation) relates to a method for maintaining an intact, non-degraded molecular complex of factor VIII (FVIII)/-von Willebrand factor (vWf) during processing of blood, plasma and plasma fractions further containing cellular sources of a calcium ($Ca^{2+}$) activated protease capable of cleaving the FVIII/vWf complex. The functional integrity of the FVIII/vWf complex can be preserved by avoiding the action of the proteases(s) specifically on the vWf portion of the complex. The action of the calcium activated protease(s) may be avoided by removing the platelet source of the protease(s) from the plasma or by inactivating the protease (s). The protease(s) may be inactivated by removing the calcium necessary for activation, e.g. by chelation, or by inhibiting the protease(s) by specific inhibitors directed against cysteine proteases. U.S. Pat. No. 5,149,787 is thus specifically directed to a method for maintaining the von Willebrand factor portion of the FVIII/vWf complex obtained from blood or plasma.

Various solutions have been suggested to reduce the degradation by proteases of plasma derived as well as recombinant factor VIII molecules. These solutions have been directed to reduce the influence of serine and cysteine proteases, considered to be the most detrimental ones in blood plasma as well as in cell cultures. Thus, WO-A-9310143 (Johnson et al) discloses a method for recovering a purified and stabilized protein by contacting a biological sample containing factor VIII with at least one protease inhibiting or protease removing agent. The method is particularly directed to inhibit or remove thrombin, since factor VIII is said to be very sensitive to minute quantities of this serine protease naturally present in blood plasma. The protease inhibitors include e.g. benzamidine, antithrombin III, heparin and hirudin. The effect of the method is only shown for plasma derived factor VIII.

WO-A-9002175 (Novo-Nordisk) discloses a method for producing polypeptides by culturing eukaryotic cells in the presence of protease inhibitors. Specific examples include factor VIII as the polypeptide, but the protease inhibitors are all directed to serine and cysteine proteases and the inhibitors are present in the cell culture per se.

The problem encountered with metal-dependent proteases in the production of various proteins, has been much less surveyed than the role of serine and cysteine proteases. More particularly, this specific problem has never been addressed previously in connection with factor VIII. The aim of the present invention is therefore to counteract the influence of metal-dependent proteases in production of recombinant factor VIII, in such a way that essentially all factor VIII activity obtained after harvest is retained throughout the purification process.

DESCRIPTION OF THE INVENTION

An object of the present invention is to reduce the influence of metal-dependent proteases on recombinant factor VIII, by inhibiting the action of the metal-dependent proteases per se.

A further object of the of the present invention is to reduce the influence of metal-dependent proteases on recombinant factor VIII, by inhibiting the action of or removing the metal ions required for activity of these proteases.

Another object of the present invention is to provide an efficient purification process, where the activity of recombinant factor VIII is essentially retained.

Yet another object of the present invention is to provide an efficient process, for producing a highly concentrated and very pure solution of recombinant factor VIII.

The objects above are met by the present invention, which relates to a process for reducing the degradation of recombinant coagulation factor VIII caused by metal-dependent proteases, wherein an inhibitor of metal-dependent proteases is added to a solution after harvest, and in that the inhibitor is selected from the group consisting of i) complexing agents with a stronger affinity for the alkaline-earth metal ion or metal ion of the protease than for the ion or ions stabilizing the factor VIII molecule and ii) compounds structurally related to the natural substrate of the protease and containing an electronegative moiety.

The inventors of the present invention have found that certain inhibitors of metal-dependent proteases have a surprisingly positive impact on the activity of recombinant factor VIII in and after the purifying sequence. The presence of these inhibitors makes it possible to efficiently inhibit the action of the metal-dependent proteases per se and/or inhibit the action of or remove the metal ions required for activity of the proteases particularly detrimental to the recombinant factor VIII molecule. In this way, the influence of these metal-dependent proteases can be reduced, giving essentially retained factor VIII activity throughout the entire purification process.

The metal-dependent proteases are either considered to be metal-activated proteases (to which metal ions must be added for activity) or metallo proteases (which contain metals as an integral part of their structure). Concerning the first group, activation and stabilization of enzymes by metals frequently occur in several classes of proteases, such as serine and cystein proteases. For example, in the field of blood functions, especially coagulation, fibrinolysis, and complement activation, a group of vitamin K-dependent calcium-binding domains are common (see e.g. László Patthy in Methods in Enzymology, 222, p. 10–21 (1993)). Concerning the latter metallo proteases, a review of mammalian metalloendopeptidases, being an important subgroup of this protease class, can be found in Bond et al, Int. J. Biochem., 17, no. 5, p. 565–574 (1985). These authors conclude, that $Zn^{2+}$ appears to be the essential metal for all of the characterized mammalian metallo proteases. In a more recent review (D. A. Auld, Methods in Enzymology, 248, p. 229–242 (1995)) this ion is still considered to be the active ion of an overwhelming majority of the metallo proteases. This does not exclude a structural and functional role also of other metals, like $Cu^{2+}$, $Fe^{2+}$, $Fe^{3+}$, $Mn^{2+}$, $Co^{2+}$ and $Cd^{2+}$ (Auld, see above). Thus, an enzyme dependent on $Zn^{2+}$ as well as $Ca^{2+}$, is described in Butler et al, Biochem. J., 241, p. 229–235 (1987).

In the present invention, the term after harvest relates to process activities and steps after separation of cells from the conditioned medium, e.g. by centrifugation and/or filtration. In the present invention, the inhibitor of metal-dependent proteases can be added to any solution obtained or used after harvest. It is however preferred to add the inhibitor to a solution selected from the group consisting of the harvest solution and any aqueous solution being fed to or leaving the primary isolation. More particularly, in the present invention, the inhibitor can be present in the harvest solution, in the optionally preconcentrated aqueous solution containing factor VIII before loading, in the washing liquid, in the elution liquid, in the solution resulting from the primary isolation, or a combination thereof. If the primary isolation is a chromatography step, the solution resulting from the primary isolation is termed eluate. If the inhibitor is added to the solution resulting from the primary isolation, the addition is made before the solution is brought to the next process step. In this way, it is possible to considerably reduce the content of degraded factor VIII molecules.

In the present invention, factor VIII is recombinant and it can be full-length factor VIII or preferably a deletion derivative of full-length factor VIII having coagulant activity. By deletion derivative is here meant coagulation factor VIII, in which the whole or part of the B-domain is missing, while the coagulant activity is retained. The structure and biochemistry of recombinant factor VIII products in general have been described by Kaufman in Trends in Biotechnology, 9, p. 353–359 (1991) and Hematology, 63, p. 155–65 (1991).

Factor VIII concentrates derived from human plasma contain several fragmented fully active factor VIII forms as described by Andersson et al, Proc. Natl. Acad. Sci. USA, 83, p. 2979–83 (May 1986). The smallest active form has a molecular mass of 170 kDa and consists of two chains of 90 kDa and 80 kDa held together by metal ion(s). Reference is here made to EP-A-0 197 901 (Pharmacia AB).

Pharmacia AB of Stockholm, Sweden, has developed a recombinant factor VIII product which corresponds to the 170 kDa plasma factor VIII form in therapeutic factor VIII concentrates. The truncated recombinant factor VIII molecule is termed r-VIII SQ and is produced by Chinese Hamster Ovary (CHO) cells in a cell culture process in serum-free medium. The structure and biochemistry of r-VIII SQ have been described in WO-A-9109122 (Pharmacia AB). In the present invention, more preferably the deletion derivative is recombinant factor VIII SQ (r-VIII SQ).

Suitably, the conditioned medium obtained after harvesting the cell culture when producing the recombinant coagulation factor VIII according to the present invention is essentially free of the von Willebrand factor (vWf), and preferably totally free thereof. It is more preferred that the cell culture used for producing the recombinant coagulation factor VIII is essentially free of the von Willebrand factor (vWf), and preferably totally free. In this way, the entire process for producing the recombinant factor VIII is free of vWf. This makes possible production of a factor VIII with a very high activity.

Many proteins contain ions of alkaline earth metals or metals. This is also valid for the factor VIII molecule, requiring a bridge of at least one divalent ion, for reasons of structural integrity and retained activity. This ion is generally considered to be calcium. However, in tests in-vitro various divalent ions have been used to advantage, e.g. calcium, manganese, cobalt, or a combination thereof. Reference is here made to Andersson et al (see above), Nordfang et al, J. Biol. Chem., 263, p. 1115–1118 (1988) and Fay et al in J. Biol. Chem., 267, p. 13246–13250 (1992). Recently, the content of copper in factor VIII has been revealed by N. Bihoreau et al in Eur. J. Biochemistry, 222, p. 41–48 (1994). The authors suggest that the presence of this cation is not directly related to the coagulant activity but is of structural importance for the molecule. However, Nordfang et al (see above) failed when attempting to reassociate dissociated factor VIII chains by addition of copper.

The presence of a divalent ion, such as calcium, makes factor VIII a protein particularly sensitive to the presence of complexing agents which tend to trap ions of alkaline earth metals or metals. Thus, to cite Bo Ersson et al in Protein Purification; Principles, High Resolution Methods, and Applications, VCH Publishers, Inc., New York, p. 7–10 (1989): "Many proteins are stabilized by calcium ions. The divalent ions calcium and magnesium are trapped by EDTA and cannot be used in combination with this chelator".

In Andersson et al (see above), thorough tests were carried out to determine the role of metal ions in the structure of factor VIII derived from human plasma. The results showed that EDTA dissociated the 80 kDa doublet chain from each of the heavier chains having molecular sizes from 200 to 90 kDa. The presence of chelators caused dissociation of the dimer subunits as disclosed also by Fay et al (see above).

For the above reasons, it is especially surprising that complexing agents can be present in a factor VIII solution, without destabilizing the factor VIII molecules to any appreciable extent. Thus, contrary to the previous belief complexing agents can be used to advantage in a process for purifying recombinant factor VIII.

In the present invention, the inhibitors for metal-dependent proteases are selected from i) complexing agents with a stronger affinity for the metal ion of the protease than for the ion or ions stabilizing the factor VIII molecule and ii) compounds structurally related to the natural substrate of the protease and containing an electronegative moiety. Compounds from the latter group are suitably peptides or peptide analogues, preferably selected from the group consisting of hydroxamates, phosphoramidates and carboxylates. The mechanism for the inhibition of metallo proteases by peptides or peptide analogues functionalized with e.g. hydroxamates, phophoramidates or carbonyl groups is not fully clear. However, in the literature their effect is considered to be due to a chelating function (see especially p. 221–222 of Birkedal-Hansen et al, Critical Review in Oral Biology and Medicine, 4(2), p. 197–250 (1993)). Hence, the two classes of compounds which can be used as inhibitors for metal-dependent proteases according to the present invention are so closely related so as to form a single general inventive concept.

Compounds from the group of structurally related compounds can be natural, as in the case of phosphoramidon, or synthetic. The design of such synthetic inhibitors is reviewed in Bond et al (see above). One example, described by N. Nishino and J. C. Powers in Biochemistry, 17 (14), p. 2846–2850 (1978), is the synthesis of specific inhibitors for the zinc metalloendopeptidase thermolysin. In this case, the specificity of the inhibitor peptide analogue was achieved by including a hydrophobic amino acid, intended for interaction with a corresponding pocket in the active site of the enzyme, as well as a hydroxamic acid residue, for interaction with the zinc atom. An illustration of this phenomenon is given in B. Roques et al in Methods in Enzymology, 248, p. 263–283, especially p. 268–269 and 272 (1995)). Further examples of hydroxamates are disclosed in WO 90/05719.

In the present invention, the inhibitor of metal-dependent proteases is suitably a complexing agent. In the following, therefore, the invention will be described with reference to complexing agents as inhibitors of metal-dependent proteases. The selection of complexing agent in the present invention is e.g. dependent upon the affinity for the various relevant ions, concentration required, toxicity and cost. The complexing agents of the present invention have a higher affinity for the metal ion of the protease than for the ion or ions stabilizing the factor VIII molecule. The ranking of affinity is here aimed at the actual metal chelating equilibrium situation, i.e. related to the strength of the binding between the actual ions and the chelating sites in the actual proteins. This should be compared to the strength of the binding between these ions and the added complexing agent. Furthermore, the equilibrium situation should be related to the actual ionic strength, pH and other physico-chemical factors of importance.

Complexing agents suitable in the present invention include nitrogenous polycarboxylic acids, heterocyclic amines, phenanthrolines, pyridine carboxylic acids, quinolines, salicylates, N-acyl derivatives of collagen, N-aminoacyl derivatives of β-diketones, thiol compounds and di- and tricarboxylic acids. Examples of nitrogenous polycarboxylic acids are ethylenediamine tetraacetic acid (EDTA), [ethylenedioxy)diethylenedinitrilo]tetraacetic acid (EGTA) and nitriloacetic acid (NTA). Examples of heterocyclic amines are imidazole and L-histidine. Examples of phenanthrolines are 1,10-phenanthroline and methyl-derivatives of phenanthroline. Examples of pyridine carboxylic acids and quinolines are pyridine-2,6-dicarboxylic acid (dipicolinic acid) and 8-hydroxyquinoline. Examples of di- and tricarboxylic acids are oxalic acid and citric acid. Other examples are disclosed in David Auld (see above, especially in Table I) and Vincent H. L. Lee, J. Cont. Release, 13, p. 213–223 (1990). For reasons of affinity toward the metal ion or ions of the protease as well as toward the ion or ions stabilizing the factor VIII molecule, and for reasons of toxicity, simplicity and economy, it is preferred to use EDTA in the present invention. Of the various salts of EDTA it can be advantageous to use a salt containing at least one of the ions stabilizing the factor VIII molecule, e.g. the calcium and sodium salt of EDTA. Data for toxicity and other properties of the di- and trisodium salts of EDTA as well as the corresponding calcium disodium salt can be found in the Merck Index, Merck & Co., Inc., Rahway, N.J., USA, 11th ed., p. 550, (1989), and Martindale, The Extra Pharmacopoeia, Pharmaceutical Press, 30th ed., p. 681–682 and 693–694 (1993).

The concentration of the complexing agent should be regulated such that the ion or ions stabilizing factor VIII still can be detected as free ions in the solution at issue. This makes possible retained activity of the factor VIII molecules. The total concentration of the ion or ions stabilizing factor VIII is suitably at least about 0.2 mM, preferably in the range of from 1 up to 300 mM and more preferably in the range of from 5 up to 50 mM. The concentration is independent of the point of addition, but is dependent upon the concentration of complexing agent.

When the complexing agent is a nitrogenous polycarboxylic acid and added to the harvest solution, the concentration of complexing agent should be in the range of from about 0.01 up to about 10 mM, suitably from 0.1 up to 5 mM and preferably from 0.3 up to 3 mM.

When the complexing agent is a nitrogenous polycarboxylic acid and added to a liquid used for washing in the primary isolation, the concentration of complexing agent should be in the range of from about 0.01 up to about 50 mM, suitably from 0.1 up to 10 mM and preferably from 0.5 up to 5 mM.

When the primary isolation is a chromatography step, the concentration of a nitrogenous polycarboxylic acid as complexing agent in the liquid used for eluting the adsorbed factor VIII molecules should be in the range of from about 0.1 up to about 30 mM, suitably from 0.5 up to 15 mM and preferably from 1 up to 5 mM.

When the complexing agent is a nitrogenous polycarboxylic acid and added to the solution resulting from the primary isolation, the concentration of complexing agent should be in the range of from about 0.1 up to about 30 mM, suitably from 0.5 up to 15 mM and preferably from 1 up to 5 mM.

When the complexing agent is a compound other than a nitrogenous polycarboxylic acid, it lies within the competence of the skilled person to arrive at suitable concentrations for performing the present invention. For example, when using phenanthroline, the concentration required may be double that of the nitrogenous polycarboxylic acids. With the heterocyclic amines histidine and imidazole, the concentration may be even higher, especially with imidazole, being the weaker complexing agent.

The primary isolation of the present invention can be any process step aimed at increasing the concentration of factor VIII in the harvest solution. Suitable and well known examples include chromatography steps, ultrafiltration, precipitation e.g. with ammonium sulfate and the like. The chromatography steps include cation exchange, anion exchange, affinity and hydrophobic interaction chromatography steps. In the present invention, it is especially advantageous to use an ion-exchange chromatography step as primary isolation. This is because ion-exchange gels are rigid allowing for treatment with strong alkaline solutions to restore the adsorbing capacity, if the gel surface is still contaminated after elution. In preferred embodiments, the primary isolation is a cation-exchange chromatography step. The use of a cation-exchange step as the primary isolation, allows for an immediate and dramatic reduction in liquid volume and total protein content of the harvest solution. This is particularly true if albumin is present in the harvest solution. Thus, with a cationic gel the albumin is not adsorbed to the gel surface to any substantial degree, and can be easily removed by washing, as opposed to an anionic gel.

Cation-exchange gels of various types can be used in the present invention. The ligands are suitably selected from the group consisting of sulfoethyl, sulfopropyl, sulfobutyl, sulfonate, and carboxymethyl. Preferably, the ligand is sulfopropyl or sulfonate since this allows for a wide pH range. Characteristics of suitable cation-exchange gels can be found in Protein Purification; Principles, High Resolution Methods, and Applications, VCH Publishers, Inc., New York, p. 107–148 (1989) and E. Boschetti, J. Chromatogr., A 658, 1994, p. 207–236, which are hereby incorporated by reference. The matrix can be selected from various strongly hydrophilic matrices e.g. agarose matrices such as a wide variety of SEPHAROSE® matrices sold by Pharmacia Biotech of Uppsala, Sweden, organic polymer matrices such as TSK-GEL:s sold by Tosoh Corp. of Tokyo, Japan, or highly porous organic polymer matrices sold by Per Septive Biosystems of Boston, USA. Membrane matrices are also suitable, e.g. SARTOBIND® sold by Sartorius of Germany and MEMSEP® sold by Millipore of USA. The matrix is preferably an agarose matrix. Suitable agarose matrices in the present invention are, apart from SEPHAROSE®, MINILEAK® sold by Kem-En-Tec A/S of Copenhagen, Denmark and Bio-Gel A sold by Bio-Rad, of Brussels, Belgium. Preferably, the matrix is cross-linked allowing for a fast flow (FF) and thereby high production capacity. More preferably, chromatography of the present invention is carried out on a SP SEPHAROSE® FF gel.

In the following, the invention will be described using a cation-exchange step as primary isolation. When the primary isolation is a different step, it lies within the competence of the skilled person to arrive at suitable conditions for performing the present invention. This applies e.g. to pH and ionic strength of the various solutions as well as process temperature.

The ionic strength of the solution being loaded onto the cation-exchange resin as well as the ionic strength of the eluting solution, are important for the type of purification obtained as well the efficiency of the purification. Thus, to make possible an efficient separation primarily of factor VIII and impurities, the ionic strength of the solution being loaded onto the cation-exchange resin and/or a solution used for washing factor VIII adsorbed to the cation-exchange resin, should be in the range of from about 0.05 up to about 0.3M, suitably from 0.1 up to 0.25M, and preferably from 0.15 up to 0.2M. The ionic strength of the solution used for eluting factor VIII from the cation-exchange resin should be at least about 0.3M when the elution is commenced, suitably in the range of from 0.4 up to 2M, and preferably from 0.5 up to 0.9M. The ionic strength can be kept constant throughout the elution, or increased linearly or step-wise or combinations thereof.

The ionic strength of the solution being loaded onto the cation-exchange resin as well as the solution used to eluate factor VIII, are suitably obtained by the presence of an alkali metal chloride, e.g. sodium chloride or potassium chloride, or ammonium acetate, or any combination thereof.

The solution being loaded onto the cation-exchange resin for adsorbing factor VIII to the gel surface as well as the solution used for eluting the factor VIII molecules from the gel surface, should have a pH in the range of from about 5 up to about 8, suitably from 5.4 up to 7.0.

With the present invention, the process temperature is less critical than with the prior art techniques, where a temperature well below ambient temperature was deemed necessary to avoid excessive loss in yield. With the present invention it is possible to run the primary isolation as well as the subsequent process steps at ambient temperature, without risking severe destabilization of the factor VIII molecules. Thus, adsorption as well as desorption of factor VIII in a cation-exchange step, can be carried out at a temperature of e.g. 18 up to 25° C. It is, however, suitable to adsorb as well as desorb out at a temperature below ambient, preferably at a temperature in the range of from about 2° C. up to about 10° C.

In the present invention, the cation-exchange chromatography step can be repeated, to give totally two, three or even more cation-exchange steps in a purification sequence. The use of several cation-exchange steps can reduce the content of impurities further, and at the same time increase the concentration of factor VIII. These and other advantages, of course, have to be weighed against the increase in apparatus costs. If at least two cation-exchange steps are used, they can be used with or without intermediate process steps.

The following examples are intended to further illustrate the present invention, without limiting the scope of the invention.

EXPERIMENTAL

Preparation of Recombinant Factor VIII

The production of recombinant factor VIII SQ (r-VIII SQ) was essentially performed as described in patent WO-A-9109122, example 1–3. A DHFR deficient CHO cell-line (DG44N.Y.) was electroporated with an expression vector containing the r-VIII SQ gene and an expression vector containing the dihydrofolate-reductase gene. Following selection on selective media surviving colonies were amplified through growth in stepwise increasing amounts of methotrexate. Supernatant from the resulting colonies were individually screened for factor VIII activity. A production clone was chosen and this was subsequently adapted to serum free suspension growth in a defined medium and finally a large scale cell cultivation process was developed. Supernatant is collected after certain time periods and further purified as described below.

Example 1

The efficiency of the present invention was established by determination of proteolytic activity modified according to Twining and disclosed in Boehringer Mannheim Biochemica. The method chosen was a protease assay with casein which was resorufin-labeled. By treatment with proteases, resorufin-labeled peptides are released from the casein. The concentration of these resorufin-labeled peptides in the supernatant is a measure of the proteolytic activity present. The test sample was incubated at 37° C. for a period of time which was dependent upon the sample at issue. The absorption wave-length chosen was 574 run throughout the tests.

The conditioned medium (containing human serum albumin) was clarified and the disodium salt of EDTA was subsequently added in an amount ranging from 0.23 mM up to 23 mM.

Preincubation of the conditioned medium with or without EDTA was conducted at 37° C. for 2 h. After the addition of substrate, further incubation was carried out for 17 h. The pH in the incubation mixture was 7.5.

Absorbance corrected, refers to the absorption after subtraction of the blank value. The results are given in the following Table.

TABLE I

Protease activity in a harvest solution with and without EDTA

| Experiment no. | EDTA mM | Mean absorbance | corrected | Protease activity (%) |
|---|---|---|---|---|
| 1 | 0 (Blank) | 970 | 0 | — |
| 2 | 0.23 | 1835 | 865 | 43 |
| 3 | 1.2 | 1141 | 171 | 8 |
| 4 | 2.3 | 1069 | 99 | 5 |
| 5 | 11.5 | 994 | 24 | 1 |
| 6 | 23 | 933 | −37 | −2 |

As is evident from the Table, the addition of a complexing agent to a harvest solution dramatically reduces the protease activity. The experiments were repeated twice and the results obtained were well in agreement with the results disclosed in Table I.

Example 2

Conditioned medium (containing human serum albumin) was clarified and imidazole subsequently added in an amount ranging from 3.6 mM up to 360 mM.

The preincubation, incubation and the tests of relative protease activity were carried out according to Example 1. The results are given in the following Table.

TABLE II

Protease activity in a harvest solution with and without imidazole

| Experiment no. | EDTA mM | Mean absorbance | corrected | Protease activity (%) |
|---|---|---|---|---|
| 1 | Blank | 970 | 0 | — |
| 2 | 3.6 | 2891 | 1921 | 95 |
| 3 | 18 | 2985 | 2015 | 100 |
| 4 | 36 | 3190 | 2220 | 110 |
| 5 | 180 | 1258 | 288 | 14 |
| 6 | 360 | 1143 | 173 | 9 |

As is evident from the Table, the addition of a complexing agent to a harvest solution dramatically reduces the protease activity.

Example 3

Conditioned medium (containing human serum albumin) was clarified and histidine subsequently added in an amount ranging from 0.14 mM to 13.6 mM.

The preincubation, incubation and the tests of relative protease activity were carried out according to Example 1. The results are given in the following Table.

TABLE III

Protease activity in a harvest solution with and without histidine

| Experiment no. | Histidine mM | Mean absorbance | corrected | Protease activity (%) |
|---|---|---|---|---|
| 1 | Blank | 970 | 0 | — |
| 2 | 0.14 | 2561 | 1591 | 79 |
| 3 | 0.7 | 2857 | 1887 | 94 |
| 4 | 1.4 | 3153 | 2183 | 108 |
| 5 | 7 | 1495 | 525 | 26 |
| 6 | 13.6 | 1684 | 714 | 35 |

As is evident from the Table, the addition of a complexing agent to a harvest solution dramatically reduces the protease activity.

Example 4

Conditioned mediums (containing human serum albumin) from two consecutive harvests, were clarified and buffered with $NH_4Ac$. Each resulting solution, with a pH of 6.8, was loaded onto a column containing SP SEPHAROSE® FF sold by Pharmacia AB of Uppsala, Sweden. This cation-exchange chromatography step was performed at about 8° C. After washing, factor VIII was eluted with a salt buffer containing 0.8M NaCl and 0.1M $NH_4Ac$. The washing liquid as well as the elution liquid contained 3 mM EDTA in the tests with harvest solution no. 2. Tests without EDTA present was carried out for comparison (harvest solution no. 1). The preincubation, incubation and the tests of relative protease activity were carried out according to Example 1, except that the incubation time was 2 h. The concentration of unbound $Ca^{2+}$-ions was determined by an ion-selective electrode. The results are given in the following Table.

TABLE IV

Protease activity after elution from a SP Sepharose ® FF as primary isolation

| Harvest solution no. | EDTA mM | Mean absorbance | corrected | Protease activity (%) | Unbound Ca$^{2+}$ ions (mM) |
|---|---|---|---|---|---|
| — | Blank | 0.041 | 0 | | — |
| 1 | 0 | 0.324 | 0.283 | 100 | 44 |
| 2 | 3 | 0.064 | 0.023 | 8 | 25 |

As is evident from the Table, the addition of a complexing agent to a washing and elution liquid dramatically reduces the protease activity.

Example 5

Conditioned mediums (containing human serum albumin) from four harvests being different from the previous Examples were clarified and buffered with NH$_4$Ac. Each resulting solution, with a pH of 6.8, was loaded onto a column containing SP SEPHAROSE® FF. This cation-exchange chromatography step was performed at about 8° C. After washing, factor VIII was eluted with a salt buffer containing 0.8M NaCl and 0.1M NH$_4$Ac. The washing liquid as well as the elution liquid contained 3 mM EDTA. Tests without EDTA present were carried out for comparison. The procoagulant activity of factor VIII was determined by use of a chromogenic substrate method, COATEST® Factor VIII kit (Chromogenix AB of Sweden) after storage at ambient temperature for up to 24 hours. The relative standard deviation (RSD) of the method is 7%. The results are given in the following Table.

TABLE V

Stability of factor VIII after elution from a SP SEPHAROSE ® FF as primary isolation followed by storage at ambient temperature

| Comparing experiment No | Harvest solution No | Storage time for S-eluate (h) | Factor VIII activity (%)[1] In preparation without EDTA | In preparation with 3 mM EDTA |
|---|---|---|---|---|
| A | 1 | 0 | 100 | 100 |
|   | 1 | 6 | 96 | 98 |
|   | 1 | 24 | 84 | 100 |
| B | 2 | 0 | 100 | 100 |
|   | 2 | 6 | 82 | 101 |
|   | 2 | 24 | 15 | 98 |
| C | 3 | 0 | 100 | 100 |
|   | 3 | 6 | 89 | 109 |
|   | 3 | 24 | 29 | 109 |
| D | 4 | 0 | 100 | 100 |
|   | 4 | 6 | 81 | 103 |
|   | 4 | 24 | 15 | 102 |

[1] as compared to the zero-time value for each storage series

As is evident from the Table, the addition of a complexing agent to a washing and elution liquid dramatically increases the possibility to maintain the activity of factor VIII.

Example 6

A conditioned medium (containing human serum albumin) from a different harvest than the previous Examples, was clarified and buffered with NH$_4$Ac. The resulting solution, with a pH of 6.8, was loaded onto a column containing SP SEPHAROSE® FF. This cation-exchange chromatography step was performed at about 8° C. After washing, factor VIII was eluted with a salt buffer containing 0.4M NaCl and 0.1M NH$_4$Ac. After elution, various amounts of EDTA were added to the resulting solution. Tests without EDTA present were carried out for comparison. The procoagulant activity of factor VIII was determined after storage at ambient temperature for up to 246 hours, in accordance to the procedure described in Example 5. The results are given in the following Table.

TABLE VI

Activity of factor VIII in % of the initial value after addition of EDTA to an eluted solution from a SP SEPHAROSE ® FF as primary isolation

| EDTA (mM) | Storage time (h) | | | | | | | |
|---|---|---|---|---|---|---|---|---|
| | 0 | 2.5 | 5 | 10 | 24 | 48 | 72 | 100 | 246 |
| 0 | 100 | 79 | 55 | 30 | 1.7 | | | | |
| 0.01 | 100 | 77 | 59 | 32 | 1.9 | | | | |
| 0.03 | 100 | 76 | 59 | 33 | 2.1 | | | | |
| 0.1 | 100 | 82 | 65 | 43 | 4.6 | | | | |
| 0.3 | 100 | 79 | 71 | 55 | 11 | | | | |
| 1.0 | 100 | 90 | 97 | 97 | 75 | 54 | | | |
| 3.0 | 100 | 92 | 102 | 104 | 100 | 96 | 80 | 91 | 72 |

As is evident from the Table, the addition of a complexing agent to a solution already eluted from a cation-exchange resin, dramatically increases the possibility to maintain the activity of factor VIII.

Example 7

A conditioned medium (containing human serum albumin) from a different harvest than the previous Examples, was clarified and buffered with NH$_4$Ac. The resulting solution, with a pH of 6.8, was loaded onto a column containing SP SEPHAROSE® FF. This cation-exchange chromatography step was performed at about 8° C. After washing, factor VIII was eluted with a salt buffer containing 0.8M NaCl and 0.1M NH$_4$Ac. After elution, various amounts of EDTA were added to the resulting solution. Tests without EDTA present were carried out for comparison. The procoagulant activity of factor VIII was determined after storage at ambient temperature for up to 28 hours, in accordance to the procedure described in Example 5. The results are given in the following Table.

TABLE VII

Activity of factor VIII in % of the initial value after addition of EDTA to an eluted solution from a SP SEPHAROSE ® FF as primary isolation

| EDTA (mM) | Storage time (h) | | |
|---|---|---|---|
| | 0 | 5 | 28 |
| 0 | 100 | 82 | 0 |
| 1 | 100 | 119 | 64 |
| 2 | 100 | 120 | 100 |
| 3 | 100 | 120 | 90 |
| 4 | 100 | 109 | 103 |
| 5 | 100 | 116 | 91 |

As is evident from the Table, the addition of a complexing agent to a solution already eluted from a cation-exchange resin, dramatically increases the possibility to maintain the activity of factor VIII.

Example 8

A conditioned medium (containing human serum albumin) from a different harvest than the previous Examples, was clarified and buffered with $NH_4Ac$. The resulting solution was loaded onto a column containing SP SEPHAROSE® FF. This cation-exchange chromatography step was performed at 10° C. After washing, factor VIII was eluted with a salt buffer containing 0.8M NaCl and 0.1M $NH_4Ac$. After elution, EDTA or 1,10-Phenanthroline were added to the resulting solution. The procoagulant activity of factor VIII was determined after storage at ambient temperature for up to 24 hours, in accordance to the procedure described in Example 5. The results are given in the following Table.

TABLE VIII

Stability of factor VIII after elution from a SP SEPHAROSE ® FF as primary isolation

| Experiment no. | Incubation time (h) | EDTA (mM) | Phenanthroline (mM) | Factor VIII activity (IU/ml) | (%) |
|---|---|---|---|---|---|
| 1 | 0 | 0 | 0 | 888 | 100 |
| 2 | 4.5 | 0 | 0 | 448 | 50 |
| 3 | 4.5 | 3 | 0 | 813 | 92 |
| 4 | 4.5 | 0 | 5 | 750 | 84 |
| 5 | 4.5 | 0 | 11 | 869 | 98 |
| 6 | 7.5 | 0 | 0 | 264 | 30 |
| 7 | 7.5 | 3 | 0 | 862 | 97 |
| 8 | 7.5 | 0 | 5 | 964 | 109 |
| 9 | 7.5 | 0 | 11 | 996 | 112 |
| 10 | 24 | 0 | 0 | 8 | 1 |
| 11 | 24 | 3 | 0 | 763 | 86 |
| 12 | 24 | 0 | 5 | 933 | 105 |
| 13 | 24 | 0 | 11 | 916 | 103 |

As is evident from the Table, the addition of a complexing agent to a solution already eluted from a cation-exchange resin, dramatically increases the possibility to maintain the activity of factor VIII.

We claim:

1. A process for reducing degradation of recombinant coagulation factor VIII caused by metal-dependent proteases requiring $Zn^{2+}$ for activity or containing $Zn^{2+}$ as an integral part of their structure, comprising adding an inhibitor of $Zn^{2+}$ dependent proteases to a recombinant factor VIII solution obtained after harvesting a conditioned medium from a cell culture used for producing the recombinant coagulation factor VIII, wherein the inhibitor is selected from the group consisting of
   i) complexing agents with a stronger affinity for the $Zn^{2+}$ ion of the protease than for the ion or ions stabilizing a factor VIII molecule, and
   ii) compounds structurally related to the natural substrate of the protease and containing an electronegative moiety.

2. The process according to claim 1, wherein the compound containing an electronegative moiety is selected from the group consisting of hydroxamates, phosphoramidates and carboxylates.

3. The process according to claim 1, wherein the recombinant coagulation factor VIII is produced from a cell culture essentially free of the von Willebrand factor (vWf).

4. The process according to claim 1, wherein the metal-dependent protease containing $Zn^{2+}$ as an integral part of its structure is a metalloendopeptidase.

5. A medicament for administration to a patient having the symptoms of hemophilia, comprising a therapeutically effective amount of recombinant factor VIII produced according to claim 1.

6. A method for treatment of hemophilia by administration of a therapeutically effective amount of recombinant factor VIII which has been produced according to claim 1.

7. The process according to claim 1, wherein the inhibitor is added to the harvest solution.

8. The process according to claim 7, wherein the inhibitor is a nitrogenous polycarboxylic acid in a concentration within the range of from about 0.01 to about 10 mM.

9. The process according to claim 1, wherein the inhibitor is added to a liquid and the liquid is used for washing the factor VIII molecules in a primary isolation.

10. The process according to claim 9, wherein the inhibitor is a nitrogenous polycarboxylic acid in a concentration within the range of from 0.1 to 10 mM.

11. The process according to claim 1, wherein the recombinant coagulation factor VIII is a deletion derivative of full-length factor VIII with retained coagulant activity.

12. The process according to claim 11, wherein the deletion derivative of factor VIII is deletion derivative recombinant factor VIII SQ (r-VIII SQ).

13. The process according to claim 1, wherein the complexing agent is selected from the group consisting of nitrogenous polycarboxylic acids, heterocyclic amines, phenanthrolines, pyridine carboxylic acids, quinolines, salicylates, N-acyl derivatives of collagen, N-aminoacyl derivatives of β-diketones, thiol compounds and di- and tricarboxylic acids.

14. The process according to claim 13, wherein the complexing agent is selected from the group consisting of 1,10-phenanthroline, imidazole and L-histidine.

15. The process according to claim 13, wherein the complexing agent is a nitrogenous polycarboxylic acid.

16. The process according to claim 15, wherein the nitrogenous polycarboxylic acid is ethylenediamine tetraacetic acid (EDTA).

17. The process according to claim 1, wherein the inhibitor is added to a solution selected from the group consisting of the harvest solution and an aqueous solution being fed to or leaving a primary isolation.

18. The process according to claim 17, wherein the inhibitor is added to a solution resulting from the primary isolation.

19. The process according to claim 17, wherein the inhibitor is added to an elution liquid used to eluate factor VIII.

20. The process according to claim 19, wherein the inhibitor is a nitrogenous polycarboxylic acid in a concentration within the range of from about 0.5 to about 15 mM.

21. The process according to claim 17, wherein the primary isolation is a chromatography step selected from the group consisting of cation exchange, anion exchange, affinity and hydrophobic interaction.

22. The process according claim 21, wherein the primary isolation is a chromatography step using a cation-exchange gel.

23. The process according to claim 22, wherein the gel comprises sulfopropyl or sulfonate ligands.

24. The process according to claim 22, wherein factor VIII molecules adsorbed to the cationic gel are eluted with a solution with an ionic strength of at least 0.3M.

25. A process according to claim 22, wherein factor VIII molecules adsorbed to the cationic gel are eluted with a solution with an ionic strength of about 0.3M.

* * * * *